United States Patent [19]

Eisinger et al.

[11] Patent Number: 4,757,019
[45] Date of Patent: Jul. 12, 1988

[54] METHOD FOR OBTAINING PURE, STABLE TISSUE CULTURES OF HUMAN MELANOCYTES

[75] Inventors: Magdalena Eisinger, Demarest; Olga Marko, Paramus, both of N.J.

[73] Assignee: Sloan-Kettering Institute for Cancer Research, New York, N.Y.

[21] Appl. No.: 845,479

[22] Filed: Mar. 27, 1986

Related U.S. Application Data

[63] Continuation of Ser. No. 469,854, Feb. 25, 1983, abandoned.

[51] Int. Cl.$^4$ ............................ C12N 5/00; C12R 1/91
[52] U.S. Cl. ............................ 435/240.21; 435/240.23; 435/948
[58] Field of Search ............... 435/240.21, 240.23, 435/29, 244, 948

[56] References Cited

U.S. PATENT DOCUMENTS

4,376,821  3/1983  Braude ................................ 435/68

OTHER PUBLICATIONS

Karasek, et al., "Isolation and Growth of Normal Human Skin Melanocytes in Cell Culture." *Journal of Investigative Dermatology*, 74:262, p. 250 (1980).

Lowe, et al., "Effects of PMA on the Phenotypic Program of Cultured Chondroblasts and Fibroblasts" *Cancer Research*, 38:2350–56 (Aug. 1978).

Cohen, et al., "Effect of a Tumor Promoter on Myogenesis" *Nature*, vol. 266 pp. 538–540 (Apr. 7, 1977).

Glimelius, et al., "Analysis of Developmentally Homogeneous Neural Crest Cell Populations in Vitro," *Chemically Abstracts* 94:97719t (1981).

Azar, et al., *Advanced Cell Biology*, pp. 234–239, Van Nostrand Reinhold Company ©1981.

Mufson, et al., "Effect of Phorbol Ester Tumor Promoters on the Expression of Melanogenesis in B-16 Melanoma Cells" *Cancer Research*, 39:3915–19 (Oct. 1979).

Madin, et al., "Established Kidney Cell Lines of Normal Adult Bovine and Ovine Origin" *Proc. of Society of Experimental Biological Medicine* v98 pp. 574–576 (1958).

Dippold, et al., "Cell Surface Antigens of Human Malignant Melanoma" *Proc. of the National Academy of Science USA*, 77(10):6114–18 (Oct. 1980).

Imai, et al. "Monoclonal Antibodies to Human Melanoma-Associated Antigens" *Transplantation Proceedings*, vol. XII, No. 3, pp. 380–383 (Sep. 1980).

Johnson, et al., "Surface Antigens of Human Melanoma Cells Defined by Monoclonal Antibodies" *European Journal of Immunology*, 11:825–831 (1981).

Kozbor, et al., "Requirements for the Establishment of High-Titered Human Monoclonal Antibodies . . . " *Journal of Immunology*, 127(4):1275–1280 (Oct. 1981).

*Primary Examiner*—Elizabeth Weimar
*Attorney, Agent, or Firm*—John P. White

[57] ABSTRACT

Human melanocyte cells are grown in tissue culture medium containing fibroblast growth suppressor plus tumor growth promoters at pH 7.2 to about 7.4. In a stepwise procedure, Langerhans, keratinocytes and most fibroblasts are removed in the presence of the above suppressor and promoter followed by a subsequent trypsinization treatment. In a final purification step, remaining fibroblasts are separated from the melanocytes by reacting the cell mixture with monoclonal antibody specific for melanocytes, and then separating out the melanocytes from the fibroblasts on density gradients.

16 Claims, 2 Drawing Sheets

Melanocytes Grown in Tissue Culture

Growth Response of Human Melanocytes to Various Compounds

METHOD FOR OBTAINING PURE, STABLE TISSUE CULTURES OF HUMAN MELANOCYTES

This invention was made with government support under National Institutes of Health (NIH) biomedical research grant 5S 07 RR 05534 and PCM 79 11 78 from the National Science Foundation (NSF). The government has certain rights in this invention.

This application is a continuation of application Ser. No. 469,854, filed Feb. 25, 1983, now abandoned.

This invention relates to tissue culture of normal human cells and more particularly to a method for the culture of purification of normal human melanocytes. Melanocytes, cultured by this method, are of use in, (1) diagnostic assays for malignancies involving melanocytes, (2) assays for toxic and/or drug agents, (3) therapy of skin disease, (4) assay for melanocyte-specific monoclonal antibodies, (5) comparison of the differentiation antigens of melanomas and melanocytes.

BACKGROUND

Current cell culture techniques grow epidermal cells in tissue culture in mixed cell populations, wherein melanocytes are only a small fraction. (Klaus, S.N. (1980) Methods Cell Biol. 21 277–288) Melanocytes in vitro are routinely taken over by keratinocytes and fibroblasts. This is a reflection of the in vivo picture wherein melanocytes exist in normal epidermis at only 1/35 the amount of keratinocytes, i.e. melanocytes are a minor component of normal epidermis.

In normal epidermis, melanocytes replicate and are shed slowly whereas keratinocytes replicate more rapidly to replace cells which have been shed.

Therefore the problems in selecting and obtaining pure melanocytes in tissue culture must overcome several obstacles attributable to melanocytes per se:

1. slow growth of the cell,
2. obtaining a sufficient supply of cells, and
3. preventing overgrowth by other cells, e.g. fibroblasts and/or keratinocytes.

These problems relate in general to other tissues where cells of interest in a mixture may be present in a low population or may be slow-growing.

SUMMARY OF THE INVENTION

The method of the invention can be used for separating out and obtaining cells of interest in pure form from tissue cultures containing a heterogeneous cell population.

In a preferred embodiment, the method of the invention is used to obtain pure human melanocytes in tissue culture. Human post-natal foreskin and facial skin are the best sources of epidermal tissue. The dermal tissue is removed entirely by forceps and trypsin; steps known in the art.

The present invention succeeds in a stepwise fashion in selecting out and purifying melanocytes, i.e. target cells, from a mixed population of epidermal cells which include fibroblasts, keratinocytes and Langerhans cells. In general, the method successfully effects use of specific growth promoters for the target cell, growth suppressor for unwanted cell types and immunoreagent specific for the target cell.

Epidermal cells are seeded and initially grown in growth medium containing PMA [phorbol 12-myristate, 13-acetate] 10 mg/ml in dimethyl sulfoxide to enhance melanocyte growth. PMA is a tumor growth promoter.

Sequential trypsinization with trypsin/ethylenediaminetetraacetic acid (EDTA) separates melanocytes from keratinocytes. This essential trypsinization step involves a brief contact of the cells with trypsin/EDTA once or twice. The enriched melanocytes, harvested after the trypsin step, are replated and grown ideally in PMA (10 ng/ml) and cholera toxin ($10^{-8}$M). Tumor growth promoter enhances melanocyte doubling time while cholera toxin suppresses fibroblast growth. Different growth promoters lead to expression of early, intermediate and late antigens on the melanocyte cell surface such as $M_3$, $M_4$, $M_5$ and $M_6$ (Table I).

A pH of 7.2 supports melanocyte growth while inhibiting that of keratinocytes. The growth medium was Eagle's minimal essential medium with 5% fetal calf serum, 2mM l-glutamine, 100 units/ml penicillin, 0.1 mg/ml streptomycin and 0.25 micrograms/ml Fungizone.

A further purification step is immune-rosetting of melanocytes with a specific mouse monoclonal antibody (mAb) which recognizes human melanocytes as opposed to keratinocytes or fibroblasts. Visualization of the antigen-antibody complex is done with sheep red blood cells coupled with Protein A. This is followed by separation of the melanocytes on a Percoll (Trademark of Pharmacia Fine Chemicals) density gradient.

The method of the present invention has overcome the aforementioned growth obstacles for melanocytes in tissue culture. This enables researchers to obtain purified melanocytes growing continuously in tissue culture. These cells serve as controls in experiments with malignant melanocytes, and further, in studies of differences between normal and malignant cells. They are also useful in experiments designed to answer questions in the area of the biology of pigment cells. Furthermore, they serve as a source for biological pigments. As a source of pigmented cells for humans they are useful for treating skin areas lacking pigment. They are also of value in treating diseases of human skin such as vitiligo, testing drugs as well as monoclonal antibodies for melanocyte specificity.

Thus, a long-time research goal of obtaining pure melanocytes for bio-medical purposes has been achieved by application of the present invention. The invention enables assay of cell samples for melanocytes. It also serves to produce melanocyte differentiation antigens.

That the method is best applied to melanocytes in tissue culture should in no way limit its use as a method for enrichment of slow growing cells or as a method for purification of a biological sample from fibroblasts. The detailed description of the invention as applied to melanocytes is for illustrative purposes only and is not meant to limit the invention. The method can be used generally to isolate and purify cell lines from a heterogeneous tissue culture containing a mixed cell population. What is effective for melanocytes can be used for tissue culture of heterogeneous cells from other tissue sources such as blood, kidney, thymus, etc. Indeed, the method is especially useful for minor or trace cells present in tissue culture, i.e. those cells normally present as only a small fraction of the overall cell population as is the case with melanocytes in epidermal tissue. The method is also useful for other slow-growing cells.

Fibroblast overgrowth of tissue culture has long been a research problem and it is especially acute with respect to slow-growing cells. Therefore, the present purification can be used to solve the fibroblast problem in many tissue culture situations where monoclonal antibody, specific for the target cell or the unwanted cell, is available.

DRAWINGS

DESCRIPTION

Figure 1:
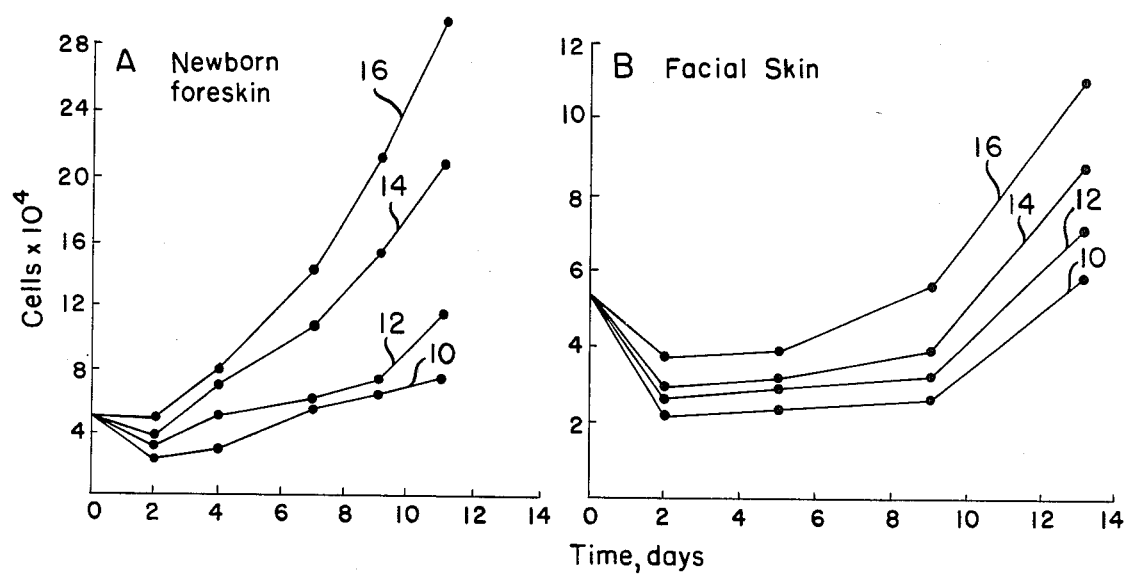
FIGS. 1A and 1B are graphs plotting the growth rate of human melanocytes in tissue culture.

Referring now to the drawing, FIG. 1 (A) shows melanocytes derived from newborn foreskins and FIG. 1 (B) shows melanocytes derived from facial skin. Both cultures were initiated with medium containing PMA (10 ng/ml) and cholera toxin (10nM) and grown in such medium for 28 days (newborn foreskin) and 8 days (facial skin).

After trypsinization, melanocytes were replated in medium: without either PMA or cholera toxin (curve 10), in medium containing cholera toxin only (curve 12), in medium containing PMA alone (curve 14), and in medium containing both PMA and cholera toxin (curve 16).

Figure 2:
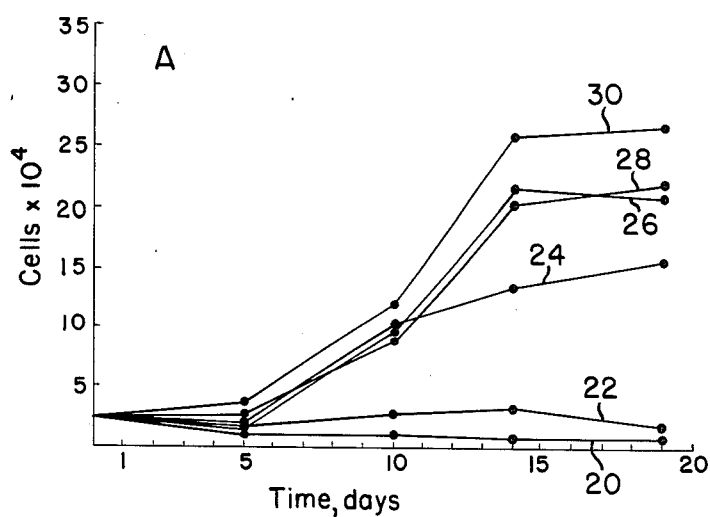
FIGS. 2A and 2B are graphs plotting the growth response of human melanocytes for various tumor promoting compounds.
Figure 2:
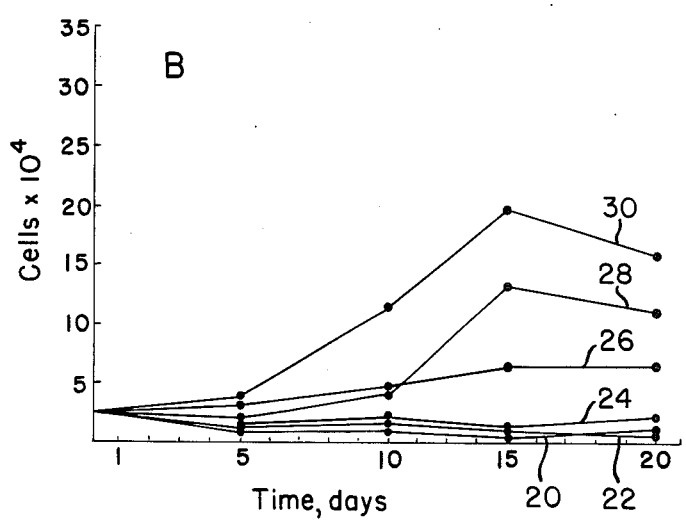

FIG. 2A plots the growth response of human melanocytes in tissue culture medium: lacking tumor promoters (curve 20); containing 4-α- phorbol didecanoate (100 ng/ml) (curve 22); containing phorbol 12-myristate 13-aetate (PMA) (10 ng/ml) (curve 24); containing mezerein (10 ng/ml) (curve 26); containing teleocidin (10 ng/ml) (curve 28); and containing PMA (10 ng/ml) plus cholera toxin ($10^{-8}$ M) (curve 30).

FIG. 2B plots the growth response of human melanocytes in tissue culture medium: lacking tumor promoters (curve 20); containing phorbol (10 ng/ml) (curve 22); containing debromoaplysiatoxin (10 ng/ml) (curve 24); containing lyngbyatoxin (10 ng/ml) (curve 26); containing phorbol dibutyrate (10 ng/ml) (curve 28); and containing aplysiatoxin (10 ng/ml) (curve 30).

The human melanocyte cell strain MC752, passage 30, was derived from a normal human foreskin specimen as previously described. The stock cultures were grown in Minimal Essential Medium (Eagle) with Earle's Salts (EMEM) containing 0.01 mM MEM nonessential amino acids (Gibco Lab, Grand Island, NY), 2 mM L-glutamine (Gibco Lab), 100 units/ml penicillin, 0.1 mg/ml streptomycin, 0.25 micrograms/ml Fungizone (Gibco Lab), 5% fetal calf serum, 10 ng/ml PMA (Consolidated Midland Corp., Brewster, NY) and $10^{-8}$ M cholera toxin (Schwartz/Mann, Orangeburg, NY), at pH 7.2. Cells were grown in this medium for 29 passages and split regularly (1:2) at weekly intervals. For specific experiments the cells were suspended with trypsin and resuspended in the above medium but in the absence of PMA and cholera toxin. The test compounds were then added at the indicated concentrations and $2.5 \times 10^4$ cells were plated in 2 ml of medium in multiwell dishes (Costar, Cambridge, MA) Trypsinized cells were counted at 5 days. Each experiment was performed in triplicate.

Epidermal single-cell Suspensions were prepared by the method of Eisinger, M., et al. (1979) Proc. Nat'l. Acad. Sc. USA 76, 5340–5344, and Madin, S. H. and Darby, N. B. (1958) Proc. Soc. Exp. Biol. Med. 98, 574–576. Also see Eisinger, et al. U.S. Pat. No. 4,254,226.

Preferred tissue sources are facial skin reduced to 15/1000 in. by means of a hand dermatome with a disposable blade, or foreskin samples freed of fatty tissue and washed with antibiotic-containing medium. In a preferred embodiment of the invention, samples were cut into 2×5 mm pieces and washed with 0.02% EDTA. 0.5–1.5g tissue were placed in 2.5 ml of 0.25% trypsin (diluted 1:250) for 12–19 hr at 4° C. Other tissue sources are adult abdominal skin, adult or fetal trunk, breast epidermis, or thigh skin.

Growth medium such as Eagle's minimal essential medium with Earle's salts/0.1mM nonessential amino acids/2mM L-glutamine/5% fetal calf serum, ph7.2, containing penicillin at 100 units/ml, streptomycin at 0.1mg/ml and Fungizone at 0.25 micrograms/ml was used to replace the trypsin. A normal tissue culture pH of 7.2 is optimal for melanocytes. This is an unexpected finding since previous tissue culture of epidermal cells proved pH 5.6–5.8 to be optimal. (Eisinger, et al, supra).

A fine forceps was used to detach the epidermis from the dermis of each piece of tissue. These isolated epidermal samples were pooled in trypsin/EDTA solution. By pippeting, single-cell epidermal suspensions were prepared. These separated epidermal cells were collected in newborn calf serum. Trypsinization of these epidermal cells was repeated until only stratum corneum cells remained essentially. These trypsinized cells were pooled, concentrated by centifugation and resuspended in tissue culture. Thus dermal tissue is entirely absent.

STEPS FOR ENRICHMENT OF MELANOCYTES

Epidermal cell suspensions were grown in tissue culture flasks at cell seeding densities of $0.8 \times 10^5$/cm$^2$ (foreskin) and $2.5 \times 10^5$/cm$^2$ (facial skin) in growth medium containing phorbol 12-myristate, 13-acetate (PMA) 10ng/ml in 0.001% dimethyl sulfoxide. PMA is also known as 12-0-tetradeconoyl phorbol 13-acetate (TPA). This compound is a murine tumor growth promoter. It also suppresses growth of keratinocytes. In some experiments cholera toxin ($10^{-8}$M) is also present at this first step.

The medium was changed 24–48 hours after cell seeding and unattached cells were removed. Then the medium was discarded 2–3 days later and the attached epidermal cells, now free of Langerhans cells, were washed, first with phosphate-buffered saline, and then with trypsin/EDTA. This selective differential trypsinization treatment step is necessary to detach melanocytes preferentially. It may be necessary to repeat this step once or twice. After this selective trypsin step, the detached melanocytes, freed of keratinocytes, are replated in gowth medium alone or in growth medium containing either 10nM cholera toxin or 10ng/ml PMA (TPA) or in growth medium containing both cholera toxin plus PMA in the aforesaid concentrations. The aforesaid concentrations are optimal. The cells are replated at $0.8-2 \times 10^4$ cells/cm$^2$ densities. In addition, other phorbol compounds as mezerein and phorbol dibutyrate (PDBu) were tested. Indole alkaloids such as teleocidin or lyngbyatoxin and polyacetates such as aplysiatoxin were tried as well. All of these aforesaid compounds have been used as tumor growth promoters. This invention uses such compounds for the first time to promote growth of a normal cell line. (See FIGS. 1 & 2).

PURE CULTURES OF CELLS FREED FROM FIBROBLASTS

For any slow-growing cell and, in the particular case of melanocyte culture, rapidly growing fibroblast cells overgrow purified melanocyte cultures even if present as a slight contaminant (0.1–1%). Preferably, monoclonal antibody which recognizes melanocytes but not fibroblasts or keratinocytes is used to purify melanocyte cultures. Mouse monoclonal antibody, $R_{24}$, recognizes antigens on melanomas and melanocytes but not antigens on fibroblasts or keratinocytes (Houghton, A. N., et al. J. Exp. Med. 156, 1755 (1982) and Dippold, W. G. et al. (1980) Proc. Nat'l. Acad. Sci. USA 77 6114–6118). The antigen is present on 94% of melanomas, 87.5% melanoma cells in culture and 84% of melanocytes. By means of the present invention, melanocytes are separated out from minor contaminants by means of an immune rosetting technique combined with a Percoll gradient. In general, this technique can be applied to purify subpopulations of cells in mixed culture. Illustration of the method for melanocytes is not meant to limit the invention. The method is especially useful where the target cell is a minor component of the cell population, or is a slow-growing cell, or where both of the aforesaid situations apply.

Hybridomas are produced by the method of Kohler and Milstein, Nature (London) 256,495–497 (1975). The antibody $R_{24}$ is produced from hybridoma cells which cells are injected intraperitoneally into Swiss Background nu/nu mice. Ascities produced by this procedure are used as the source of antibody. Dippold, W. G., et al. Supra, Houghton, A.N. et al., Supra. Also see Old, et al. Monoclonal antibodies to Cell Surface Antigens of Human Malignant Melanoma, U.S. patent application Ser. No. 307,060 filed Septs. 30, 1981 and Albino, et al. Monoclonal Antibodies Against Melanocytes and Melanomas, U.S. patent application Ser. No. 445,561, Filed Nov. 30, 1982.

The following are specific details and examples for carrying out the invention.

Protein A (PA) indicator cells are prepared by conjugating Protein A (Pharmacia) to human erythrocytes with 0.01% chromium chloride. PA cells washed 2x with antibiotic solution (1000 u/ml penicillin, 1 mg/ml streptomycin and 2.5 micrograms/ml fungizone) are suspended in a final concentration of 10% (v/v).

Melanoma cell line SK-MEL-28 was used as a reference for $R_{24}$ antibody titration. The lowest dilution of $R_{24}$ which rosetted 90–100% of the reference cells was used for melanocyte purification. This dilution was somewhere between 1/100–1/200.

Rosetting of melanocytes (1) Melanocytes collected by trypsinization as described above were washed 2× with PBS - 3% GG-free FBS [phosphate-buffered saline (without $Ca^{2+}$ or $Mg^{2+}$) containing 3% gamma globulin-free fetal bovine serum].

(2) $1 \times 10^6$ cells were distributed to 15 ml centrifuge tubes after the first wash above. After the second wash, the cells are resuspended in 300 microliters of $R_{24}$ antibody diluted in PBS-3% GG-free FBS by gentle pipetting with a Pasteur pipette. The cell-antibody suspension was then incubated at room temperature for 45 minutes with occasional shaking.

(3) The cells are then washed with PBS-3% GG-free FBS and combined with 3 ml PA cells diluted 1/100 in PBS 3% GG-free FBS. Another 45 min incubation period with gentle shaking followed for the mixture of antibody-treated target cells plus PA indicator cells, for visualization of the antigen-antibody reaction by rosette formation. Rosetted cells were counted using a hemocytometer. Then the cells were allowed to sediment; 2 ml of supernatant were removed.

Separation of cells using a Percoll density gradient:

(1) 100% solution was prepared using Percoll mixed 9:1 with 10x concentrated PBS (phosphate buffered saline $CA^{2+}$ and $Mg^{2+}$free) adjusted to PH 7.2 with $NaHCO_3$. Percoll is a trademark for colloidal silica coated with polyvinylpyrrolidone (Pharmacia Fine Chemicals)

(2) The 100% Percoll solution above was used to prepare 80%, 60%, 50% and 40% solutions with respective densities of 1.10 g/ml, 1.08 g/ml, 1.07 g/ml and 1.06 g/ml. PBS was again the solvent. 3 ml of each dilution was then successively layered into 15 ml conical tubes to form Percoll gradient. 1 ml of the cell suspension from the rosetting step was layered on top of the gradient. The gradient was centifuged in a Sorvall RC-2B centrifuge at 680g for 15 min at room temperature. Recovered cells were collected from specific fractions, diluted 1:5 in Eagle's minimal essential medium (MEM), centrifuged at 400g for 5 min followed by two further washes with MEM.

Whereas the preferred embodiment of the present invention has been described above, it is obvious that other alterations and modifications may become apparent to those skilled in the art after having read the above disclosure. It is therefore intended that the appended claims be interpreted as covering all such alterations and modifications as fall within the true spirit and scope of the invention. For example, monoclonal antibody recognizing and specific for the unwanted cell, the fibroblast in this specific example, could be used to leave the target cell free in suspension, fibroblasts being rosetted. Also, monoclonal antibody specific for melanocytes ($R_{24}$ or other) could be used to free epidermal tissue cultures of said cell.

The following are used for Identification of melanocytes:

a. Melanocytes distinguished from keratinocytes;

In tissue culture melanocytes appear bipolar or dendritic whereas keratinocytes have a round or polygonal shape. Melanin granules can be visualized under the light microscope in living tissue and when the tissue is fixed, the granules appear as 3, 4-dihydroxy phenylalanine positive cellular particles [Bakers, J. D., Jr., and Stevens, A. Eds (1977) in Theory and Practice of Histological Techniques (Churchill Livingstone, New York) P.300].

The electron microscope visualizes the melanosome and premelanosome structures in melanocytes.

b. Melanocytes distinguished from fibroblasts;

Leucine amino peptidase is an enzyme characteristic for fibroblasts, and a stain for said enzyme (Wolf, K. (1964) Arch. Kun. Exp. Dermatol. 218 446–460) revealed insignificant fibroblast contamination of these melanocyte cultures. Reliability of this marker for fibroblasts was shown by Regnier, M., et al., Acta. Dermatovener (Stockholm) 53, (1973) 241.

c. Melanocytes distinguished from Langerhans cells;

Differences in morphology (Breathnach, A.S., (1964) J. Anat. 98, 265–270), ATP-ase staining (Wachstein et al., (1960) J. Histo. Chem. Cytochem. 8, 387–388), and evaluation of Fc and complement receptors (Eisinger et al., (1979) Proc. Nat'l. Acad. Sci. USA, 76 5340-5344) serve to distinguish Langerhans and melanocyte cells.

d. DOPA staining indentifies melanomas and melanocytes Okun, et al. (1969) Theory and Practice of Histological technique (ed. J.D. Bancroft, Jr. and A. Stevens) P. 300, Churchill Livingston, New York (1977).

e. Cell surface antigens on melanocytes; Mouse monoclonal antibodies which recognize as many as 14 cell surface antigens present on human melanocyte or human melanoma cells are prepared by methods known in the art (Houghton, Supra, Dippold Supra, Albino, Supra). Some of these antigens probably distinguish early, intermediate or late stages of melanocyte differentation. Four markers of early and intermediate melanocyte differentiation characteristic for normal melanocytes antigens M-3, M-4, M-5 and M-6, could be selectively induced by some but not all of the tumor promoters (Table I). These compounds, which are potent tumor promoters on mouse skin, have been successfully used here for the first time to stimulate growth of normal human cells. Melanoma antigens M-1, M-2 and HLA-DR were not found to be induced on melanocytes by the tumor growth promoters. That the method is best illustrated by mouse tumor growth promoters is not meant to limit same only to those specific tumor growth promoters.

Best results were obtained with foreskin and facial skin as the cell sources. These tissues contain 86 90% keratinocytes, 5-7% melanocytes, and 5-7% epidermal Langerhans cells. Examination of other sources of human epidermis show lower melanaocyte concentrations ab initio, as for example 1-3% in breast epidermis. Therefore to date, post-natal foreskin and adult facial skin are the best melanocyte sources. Seeding of these cells was done at different cell densities. Lower seeding densities were used for melanocytes derived from human foreskin. It is the neonatal foreskin melanocytes which grow better and faster than those melanocytes derived from adults. Neonatal foreskin melanocytes increase 6 fold in the presence of PMA and cholera toxin but in the same 11 day period, adult sources showed only a single doubling. Higher seeding densities are necessary for adult skin. The seeding density range was $0.8-2.5 \times 10^5$ cells/cm$^2$. As noted above, an important part of this invention was the selective differential trypsinization step following cell seeding and attachment. Washing in trypsin/EDTA preferentially detaches melanocytes which are collected and further incubated after replating at cell densities of $0.8-2 \times 10^4$ cells/cm$^2$. Growth of melanocytes was also enhanced at PH 7.2 whereas keratinocytes prefer a pH of about 6.0. Thus 7.2 is an unexpected pH for epidermal cells.

PMA was selective for melanocytes at 1-10 ng/ml and as with all the tumor growth promoting substances, showed a preferential toxic effect by preventing attachment and growth of keratinocytes while stimulating those characteristics for melanocytes. It was noted that mouse monoclonal antibodies that recognize melanoctye and melanoma cell surface antigens distinguished several markers present in purified melanocyte cultures namely M-3, M-4, M-5, M-6. These presently denote early and intermediate differentiation of the cell, Houghton, et al., Supra. Not all tumor growth promoters induced all of the above-named antigens, only some of these. Aplysiatoxin, teleocidin, mezerein and PDBu showed positive effects. (See FIG. 2 and Table 1) This shows enhancement of the culture of early cells by the present method. No cell specific melanoma antigens were found on melanocytes. Melanoma cell lines can grow without the tumor growth promoters whereas the normal melanocyte criteria is dependent on such compounds for growth stimulation. This is a totally unexpected result. Other compounds tested were phorbol, 4-α-phorbol didecanoate and debronoaplysiatoxin.

Another factor which enhanced melanocyte selectively of the medium was 5% as opposed to 10% fetal calf serum. However, melanocytes will grow in 5-20% fetal calf serum.

The presence of cholera toxin suppressed the growth of fibroblasts, and therefore extended the life span of melanocytes up to 32 weeks, allowed ½ split ratio at each transfer, and permitted a 6-fold increase in the number of melanocytes. Cholera toxin alone gives a 2-fold increase in cell number.

In the presence of PMA and cholera toxin 70-90% of the melanocytes attach and grow. (See FIG. 1) Since the doubling time of melanocytes in vitro is low (every 4 days) it is essential to suppress the rapidly growing fibroblasts (doubling time 24 hrs.) and keratinocytes, as is achieved here, for the first time. The use of rosetting and Percoll gradient as a further purification step insures the absence of fibroblasts (as does the cholera toxin step before it). This $R_{24}$-Percoll step is achieved preferentially only if fibroblast contamination was less than 30% in the case of melanocyte cultures. A second use of the step was sometimes necessary to entirely free the melanocytes from fibroblasts. Even after 20 passages, melanocytes remained leucine aminopeptidase-free indicating absence of fibroblasts. The $R_{24}$-Percoll step can also be used with melanoma - fibroblast mixed cell populations even in the presence of as high as 85% fibroblasts.

In sum then, the present invention is successful in obtaining pure melanocytes in cell culture via the use of:
(1) selective tissue sources,
(2) proper PH,
(3) 5-20% fetal calf serum in the medium,
(4) selective differential trypsinization,
(5) the presence of tumor growth promoters,
(6) the presence of cholera toxin suppressor, and
(7) a further step using cell-specific monoclonal antibody and Percoll density gradient cell separation.

It was unexpected that the tumor growth promoters would be successful in the growth of a normal human cell population.

By this method, melanocytes have been obtained in culture from greater than 50 sources with melanin still present in all cells after three weeks in culture. Long-term culturing of up to eight months has been achieved. Cell viability was not affected by the presence of erythrocytes or Percoll as tested by the trypan blue exclusion test. Growth stopped when cultures reached a density of $8-11 \times 10^4$ cells/cm$^2$.

The $R_{24}$-Percoll step is unsuccessful with some melanoma cells and foreskin cells which lack $R_{24}$ antigen. Table I illustrates the Effects of Tumor Promoters on Expression of Melanocyte Differentiation Antigens Mouse monoclonal antibodies prepared as ascites from tumor-bearing mice or as hybridoma culture supernatant (Antibody M-6) were tested by mixed hemadsorption assays against the human melanocyte cell strain MC752 previously grown in the presence of the test compound (10 ng/ml) for 14 days. Human red cells were conjugated to purified anti-mouse immunoglobulin (Dako) using 0.01.% chromium chloride. Assays were performed in Falcon 3040 Microtest II plates. Sera were incubated with melanocytes for 1 hr. Target cells were then washed, indicator cells added for 1 hr and target cells evaluated for rosetting by light microscopy. Antigen expression was related to the titer endpoint giving 50% rosetted melanocytes. Titers are presented as follows: +++(>1/500,000), ++(1/50,000 to 1/500,000), +(1/100 to 1/25,000), −(<1/100).

dominal skin, facial skin, breast epidermis, adults trunk or fetal trunk, and thigh skin.

3. Method of claim 1 wherein the epidermal cells are seeded in the medium at concentration ranges of $0.8-2.5 \times 10^5$ cells/cm$^2$.

4. Method of claim 1 wherein the trypsinized melanocytes are cultured in the culture medium at concentration ranges of $0.8 \times 10^4 - 2 \times 10^4$ cells/cm$^2$.

TABLE 1

EXPRESSION OF MELANOCYTE DIFFERENTIATION ANTIGENS IN THE PRESENCE OF TUMOR PROMOTERS

| Melanoma Cell Surface Antigens | TPA + CHT | TPA | Aplysiatoxin | Teleocidin | Mezerein | PDBu | 4-α-PDD | Lyngbyatoxin | Debronotoxin |
|---|---|---|---|---|---|---|---|---|---|
| M-3 | − | − | + | + | + | + | − | − | − |
| M-4 | − | − | +++ | +++ | +++ | +++ | + | − | − |
| M-5 | − | − | ++ | ++ | ++ | + | + | − | − |
| M-6 | − | − | + | − | + | − | + | − | − |
| M-1, M-2, HLA-DR | − | − | − | − | − | − | − | − | − |
| M-9 | + | + | ++ | + | + | + | + | + | + |
| M-26 | ++ | ++ | ++ | ++ | ++ | ++ | ++ | ++ | ++ |
| M-20, M-23, M-24, M-25 M-34 | +++ | +++ | +++ | +++ | +++ | +++ | +++ | +++ | +++ |

What is claimed is:

1. Method for producing a stable, long-term culture of purified human melanocytes in tissue culture from a mixture of epidermal cells containing keratinocytes, melanocytes, Langerhans cells and fibroblast which comprises:
   (a) culturing the mixture of epidermal cells in the presence of a tumor growth promoting substance selected from the group consising of phorbol esters, indole alkaloids, polyacetates, and mixtures thereof, for a time sufficient to increase the numbers of melanocytes, decrease the number of keratinocytes, and remove the Langerhans cells from the mixture wherein the resulting epidermal cells, free of Langerhans cell, are attached to the growth vessel,
   (b) contacting the cultivated attached epidermal cell mixture with trypsin under appropriate conditions and for a time sufficient to permit detachment and separation of the melanocytes from attached keratinocytes in the attached epidermal cells,
   (c) growing the detached and separated melanocytes in a culture medium containing the tumor growth promoting substance in an amount sufficient to enhance melanocyte growth and additionally containing an amount of growth suppressor sufficient to suppress the growth of fibroblast cells,
   (d) removing fibroblasts from the cultured melanocytes by immunoreactive binding of the melanocytes with monoclonal antibody for melanocytes, and
   (e) Separating a melanocyte-monoclonal antibody product from fibroblasts.

2. Method of claim 1 wherein the human melanocytes are derived from human epidermal tissue selected from the group consisting of post-natal foreskin, adult ab- 5. Method of claim 1 wherein the normal human melanocytes produce differentiation antigens selected from the group consisting of early, intermediate and late differentiation antigens.

6. Method of claim 1 wherein the phorbol esters are selected from the group consisting of phorbol myristic acetate, (PMA) mezerein and phorbol dibutyrate.

7. Method of claim 6 wherein PMA is used in combination with cholera toxin as the fibroblast growth suppressor in the tissue culture medium for epidermal cells and separated melanocytes.

8. Method of claim 7 wherein the cholera toxin concentration is $10^{-8}$M in the culture medium.

9. Method of claim 6 wherein the PMA concentration is 1-10 ng/ml of culture medium.

10. Method of claim 1 wherein the indole alkaloids are
    selected from the group consisting of teleocidin or lyngbyatoxin.

11. Method of claim 1 wherein the polyacetate is aplysiatoxin.

12. Method of claim 1 wherein the tissue culture medium pH range is 7.2-7.4.

13. Method of claim 1 wherein the tissue culture medium is 5-20% in fetal calf serum.

14. Method of claim 1 wherein the monoclonal antibody is $R_{24}$.

15. Method of claim 1 wherein separation of the fibroblasts from the melanocyte-monoclonal antibody product is done using density gradients.

16. Tissue cell culture consisting of human melanocytes essentially free of keratinocytes, Langerhans cells and fibroblast cells as produced by the method of claim 1 and capable of growth as a biologically pure melanocyte tissue culture for at least 32 weeks or 20 passages.

* * * * *